(12) United States Patent
Chodkowski (10) Patent No.: US 10,124,137 B2
(45) Date of Patent: Nov. 13, 2018

(54) LEAK CORRECTION FOR A PATIENT INTERFACE DEVICE

(71) Applicant: KONINKLIJKE PHILIPS N.V., Eindhoven (NL)

(72) Inventor: Lauren Patricia Chodkowski, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 730 days.

(21) Appl. No.: 14/422,491

(22) PCT Filed: Aug. 22, 2013

(86) PCT No.: PCT/IB2013/056800
§ 371 (c)(1),
(2) Date: Feb. 19, 2015

(87) PCT Pub. No.: WO2014/030135
PCT Pub. Date: Feb. 27, 2014

(65) Prior Publication Data
US 2015/0217071 A1 Aug. 6, 2015

Related U.S. Application Data (60) Provisional application No. 61/691,986, filed on Aug. 22, 2012.

(51) Int. Cl.
*A61M 16/06* (2006.01)
(52) U.S. Cl.
CPC ........ *A61M 16/0622* (2014.02); *A61M 16/06* (2013.01); *A61M 16/0605* (2014.02); *A61M 16/0688* (2014.02); *A61M 16/0683* (2013.01); *A61M 2205/15* (2013.01)

(58) Field of Classification Search
CPC .............. A61M 16/06; A61M 16/0605; A61M 16/0622; A61M 16/0683; A62B 18/00; A62B 18/02; A62B 18/025; A62B 18/06; A62B 5/00; A61F 9/06; A41D 13/11
See application file for complete search history.

(56) References Cited

U.S. PATENT DOCUMENTS

| | | | |
|---|---|---|---|
| 7,640,933 B1 | 1/2010 | Ho | |
| 2005/0056286 A1 | 3/2005 | Huddart | |
| 2008/0072908 A1* | 3/2008 | Lang | A61M 16/06 128/206.21 |
| 2009/0032024 A1* | 2/2009 | Burz | A61M 16/06 128/206.24 |
| 2010/0108072 A1 | 5/2010 | D'Souza | |

(Continued)

FOREIGN PATENT DOCUMENTS

| | | | | |
|---|---|---|---|---|
| WO | WO2011060479 A1 | 5/2011 | | |
| WO | WO 2013084110 A1 * | 6/2013 | ............ | A61M 16/06 |

*Primary Examiner* — Gregory Anderson
*Assistant Examiner* — Margaret Laurca
(74) *Attorney, Agent, or Firm* — Michael W. Haas (57) ABSTRACT

A sealing device (20) includes a base (22) adapted to attach at any of a plurality of positions on a patient interface device (8), an arm (26) having a first end coupled to the base (22), and an end portion (24) connected to a second end of the base and adapted to apply pressure to an area of a cushion member (12) of the patient interface (8) device when the base is attached at any of the plurality of positions on the patient interface device.

23 Claims, 8 Drawing Sheets

(56) References Cited

U.S. PATENT DOCUMENTS

2012/0080035 A1* 4/2012 Guney ............... A61M 16/06
 128/205.25
2012/0199132 A1 8/2012 Ho

* cited by examiner

LEAK CORRECTION FOR A PATIENT INTERFACE DEVICE

CROSS-REFERENCE TO RELATED APPLICATIONS

This patent application claims the priority benefit under 35 U.S.C. § 371 of international patent application no. PCT/IB2013/056800, filed Aug 22, 2013, which claims the priority benefit under 35 U.S.C. § 119(e) of U.S. Provisional Application No. 61/691,986 filed on Aug. 22, 2012, the contents of which are herein incorporated by reference.

BACKGROUND OF THE INVENTION

1. Field of the Invention

The present invention pertains to patient interface devices structured to deliver a flow of breathing gas to a patient, and, in particular, to a sealing device to apply pressure to a selected area of a cushion member of a patient interface device to resolve a leak along the patient sealing portion of the patient interface devices.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation (NIV). It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), chronic obstructive pulmonary disease (COPD), or congestive heart failure (CHF).

Non-invasive ventilation and pressure support therapies involve the placement of a patient interface device, which is typically a nasal or nasal/oral mask, on the face of a patient to interface the ventilator or pressure support system with the airway of the patient so that a flow of breathing gas can be delivered from the pressure/flow generating device to the airway of the patient.

Typically, patient interface devices include a mask shell or frame having a cushion member attached to the shell that contacts the face of the patient. The mask shell and cushion member are typically held in place by a headgear that wraps around the head of the patient. The mask and headgear form the patient interface assembly. A typical headgear includes flexible, adjustable straps that extend from the mask to attach the mask to the patient.

Because such masks are typically worn for an extended period of time, a variety of concerns must be taken into consideration. For example, in providing CPAP to treat OSA, the patient normally wears the patient interface device all night long while he or she sleeps. One concern in such a situation is that the patient interface device is as comfortable as possible, otherwise the patient may avoid wearing the interface device, defeating the purpose of the prescribed pressure support therapy. It is also important that the interface device provide a tight enough seal against a patient's face without discomfort. A problem arises in that, in order for the mask to maintain a seal without any undue gas leaks around the periphery of the mask, the mask must be compressed against the patient's face. Conventional CPAP masks that seal by compression commonly cause uncomfortable pressure points and do not adjust well to different anatomical facial features. The conventional concept of a compression seal is to generally displace tissues on the patient's face in order to achieve a uniform seal. Tissue displacement results in pressure points, skin markings (i.e., red marks), indentations, and overall prolonged discomfort. Conventional seals also commonly distort outward upon compressing and in doing so tend to pull or push on portions of a patient's face in a manner which is uncomfortable. Such distortions can also lead to unwanted leaks.

SUMMARY OF THE INVENTION

Accordingly, it is an object of the present invention to provide a patient interface device that overcomes the shortcomings of conventional patient interface devices. This object is achieved according to one embodiment of the present invention by providing a sealing device that includes a base adapted to attach at any of a plurality of positions on a patient interface device, an arm having a first end coupled to the base, and an end portion connected to a second end of the base and adapted to apply pressure to an area of a cushion member of the patient interface device when the base is attached at any of the plurality of positions on the patient interface device.

In another embodiment, a patient interface device includes a cushion member adapted to fluidly couple with a patient interface device and adapted to contact a patient, and a sealing device. The sealing device includes a base adapted to attach at any of a plurality of positions on the patient interface device, an arm having a first end connected to the base, and an end portion connected to a second end of the arm and adapted to apply pressure to an area of the cushion member when the base is attached at any of the plurality of positions on the patient interface device.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
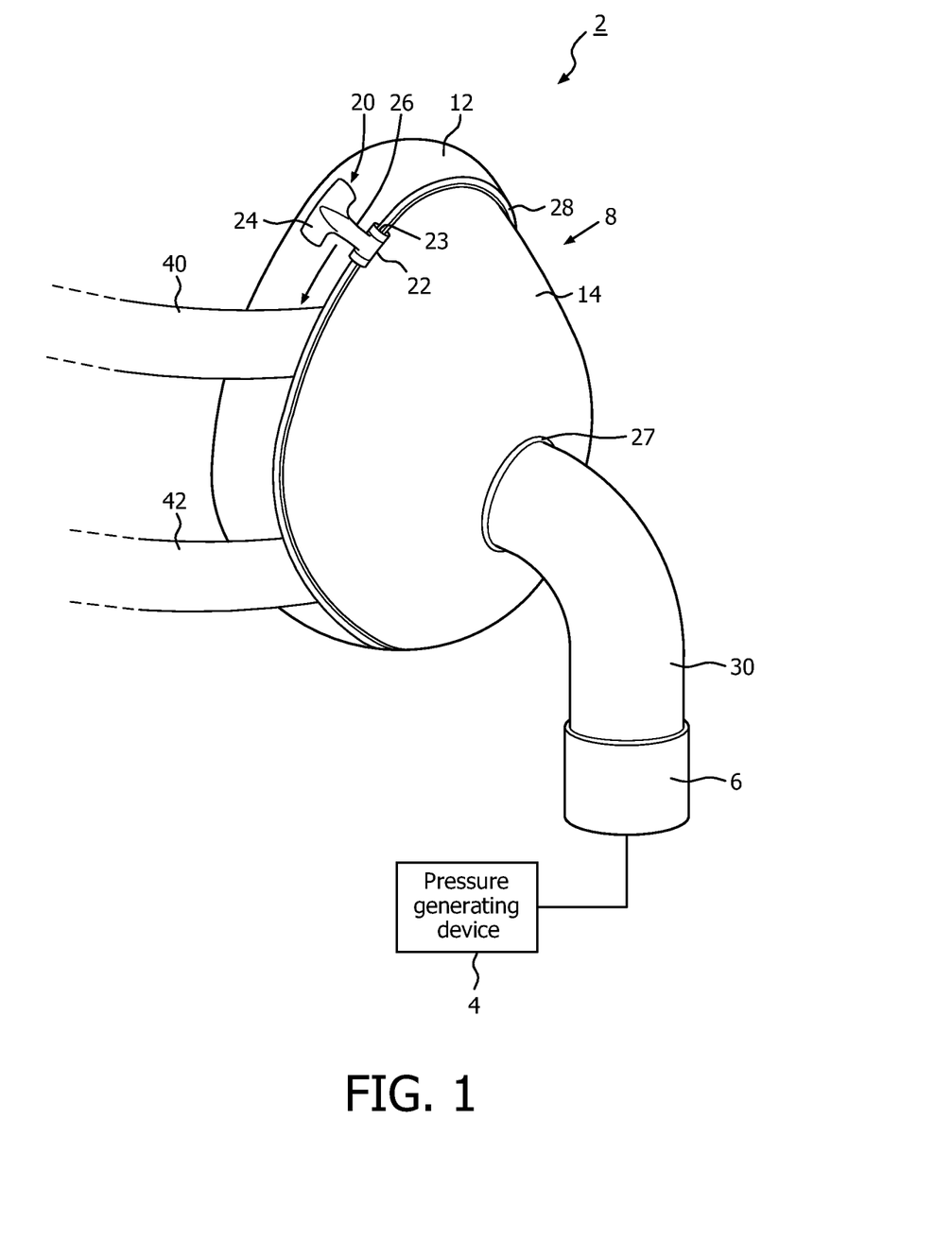
FIG. 1 is a schematic/isometric view of a system adapted to provide a regimen of respiratory therapy to a patient according to one exemplary embodiment.

FIG. 1 is a schematic/isometric view of a system 2 adapted to provide a regimen of respiratory therapy to a patient according to one exemplary embodiment of the present invention. System 2 includes a pressure generating device 4, a delivery conduit 6, and a patient interface device 8 (delivery conduit 6 and patient interface device 8 are often together referred to as a patient circuit). Pressure generating device 4 is structured to generate a flow of breathing gas and may include, without limitation, ventilators, constant pressure support devices (such as a continuous positive airway pressure device, or CPAP device), variable pressure devices (e.g., BiPAP®, BiFlex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8.

Patient interface device 8 includes a patient sealing assembly, which in the illustrated embodiment is in the form of a nasal mask. However, any type of patient sealing assembly, such as a nasal/oral mask or a full face mask, may be substituted for the nasal mask while remaining within the scope of the present invention. The patient sealing assembly includes a sealing cushion member 12 which is coupled to a faceplate 14. In the illustrated embodiment, sealing cushion member 12 is defined from a unitary piece of soft, flexible, cushiony, elastomeric material, such as, without limitation, silicone, an appropriately soft thermoplastic elastomer, a closed cell foam, or any combination of such materials.

Faceplate 14 is fluidly coupled to pressure generating device 4 through an elbow conduit 30 and delivery conduit 6. In the illustrated embodiment, faceplate 14 is made of a rigid or semi-rigid material, such as, without limitation, an injection molded thermoplastic or silicone, and includes an orifice 27 on a front end thereof and a ridge 28 on a rear end thereof. Ridge 28 extends around the outer perimeter of faceplate 14. Orifice 27 is structured to receive elbow conduit 30. The purpose of ridge 28 is described below.

Patient interface device 8 further includes an upper headgear strap 40 and a lower headgear strap 42. Upper headgear strap 40 and lower headgear strap 42 form at least a portion of a headgear assembly for securing patient interface device 8 to the head of a patient.

Patient interface device 8 still further includes a sealing device 20. Sealing device 20 includes a base 22, an end portion 24, and an arm 26 provided between base 22 and end portion 24. In the embodiment illustrated in FIG. 1, base 22 includes a c-shaped portion 23 that is structured to be selectively attached to ridge 28. Sealing device 20 can thus be selectively placed in different positions along ridge 28 so as to cause end portion 24 to apply pressure to a selected area of cushion member 12. In the exemplary embodiment, arm 26 is moveably connected to base 22 by a ratcheting mechanism that allows arm 26 and end portion 24 to move/rotate relative to base 22 and be locked in selected positions relative to each other so that a user can ratchet sealing device 20 as needed to apply pressure to a selected area of cushion member 12. Thus, when there is a leak at a selected area of cushion member 12, applying pressure to the selected area using sealing device 20 as just described resolves the leak without applying additional pressure to other areas of cushion member 12.

As noted elsewhere herein, ridge 28 is attached to faceplate 14. Ridge 28 may be permanently attached to faceplate 14 (e.g. by being adhered thereto or by being formed as an integral part thereof) or may be configured to be removable from faceplate 14. As illustrated in FIG. 1, in the exemplary embodiment, ridge 28 extends continuously around a perimeter of faceplate 14. However, it is contemplated that ridge 28 can also extend partially and/or intermittently around the perimeter of faceplate 14 and remain within the scope of the invention.

Figure 2:
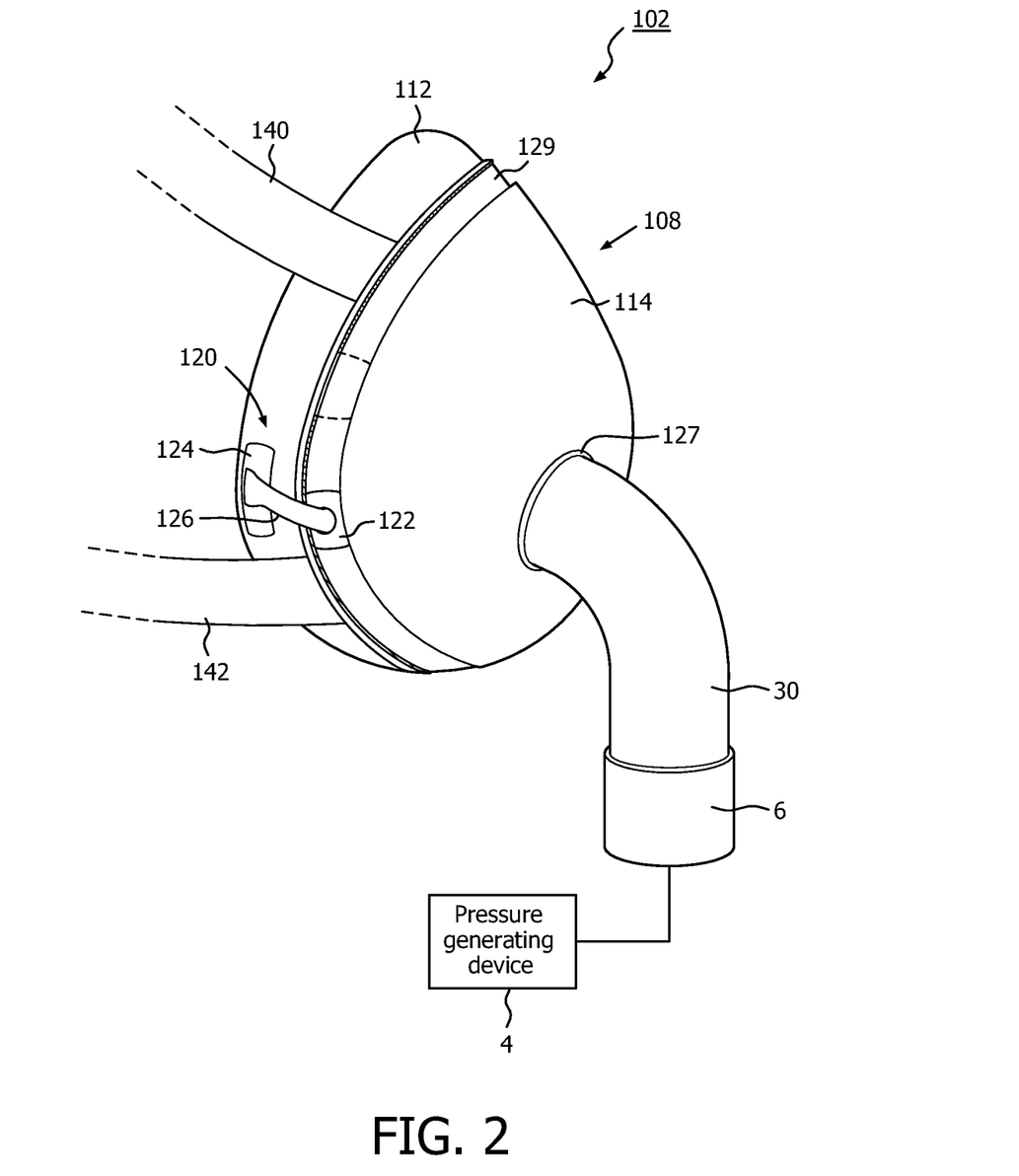
FIG. 2 is a schematic/isometric view of a system adapted to provide a regimen of respiratory therapy to a patient according to another exemplary embodiment.

FIG. 2 is a schematic/isometric view of a system 102 adapted to provide a regimen of respiratory therapy to a patient according to another exemplary embodiment of the present invention. System 102 includes pressure generating device 4, delivery conduit 6, and elbow conduit 30 which are described above with respect to FIG. 1. System 102 further includes an alternative patient interface device 108, which is described in detail below. Delivery conduit 6 is structured to communicate the flow of breathing gas from pressure generating device 4 to patient interface device 108.

Patient interface device 108 includes a patient sealing assembly, which in the illustrated embodiment is a mask in the form of a nasal mask. However, any type of patient sealing assembly, such as a nasal/oral mask or a full face mask, may be substituted for the nasal mask while remaining within the scope of the present invention. The patient sealing assembly includes a sealing cushion member 112 which is coupled to a faceplate 114. In the illustrated embodiment, sealing cushion member 112 is defined from a unitary piece of soft, flexible, cushiony, elastomeric material, such as, without limitation, silicone, an appropriately soft thermoplastic elastomer, a closed cell foam, or any combination of such materials.

Faceplate 114 is fluidly coupled to pressure generating device 4 through elbow conduit 30 and delivery conduit 6. In the illustrated embodiment, faceplate 114 is made of a rigid or semi-rigid material, such as, without limitation, an injection molded thermoplastic or silicone, and includes an orifice 127 on a front end thereof and a groove 129 on a rear end thereof. Orifice 127 is structured to receive elbow conduit 30. The purpose of groove 129 is described below.

Patient interface device 108 further includes an upper headgear strap 140 and a lower headgear strap 142. Upper headgear strap 140 and lower headgear strap 142 form at least a portion of a headgear assembly for securing patient interface device 108 to the head of a patient.

Patient interface device 108 still further includes a sealing device 120. Sealing device 120 includes a base 122, an end portion 124, and an arm 126 provided between base 122 and end portions 124. In the exemplary embodiment, end portion 124 and arm 126 form a T-shaped member. In the embodiment illustrated in FIG. 2, base 122 is configured to be inserted into groove 129. For example, and without limitation, base 122 can be configured to snap into groove 129 and/or adhesively attach to an interior of groove 129. Sealing device 120 can thus be selectively placed in different positions along groove 129 so as to cause end portion 124 to apply pressure to a selected area of cushion member 112. In an embodiment, arm 126 is not selectively movable relative to base 122. In another embodiment, arm 126 is moveably coupled to base 122 by a ratcheting mechanism that allows arm 126 and end portion 124 to move/rotate relative to base 122 and be locked in selected positions relative to one another so that a user can ratchet sealing device 120 to apply pressure to a selected area of cushion member 112. Thus, when there is a leak at a selected area of cushion member 112, applying pressure to the selected area using sealing device 120 resolves the leak without applying additional pressure to other areas of cushion member 112.

In the illustrated, exemplary embodiment, groove 129 is integrally formed in faceplate 114. It is also contemplated that groove 129 can be formed as part of a member that is separate from and attachable to faceplate 114. As illustrated in FIG. 2, groove 129 extends continuously around a perimeter of faceplate 114. However, it is contemplated that groove 129 can also extend partially and/or intermittently around the perimeter of faceplate 114 and remain within the scope of the invention.

Figure 3:
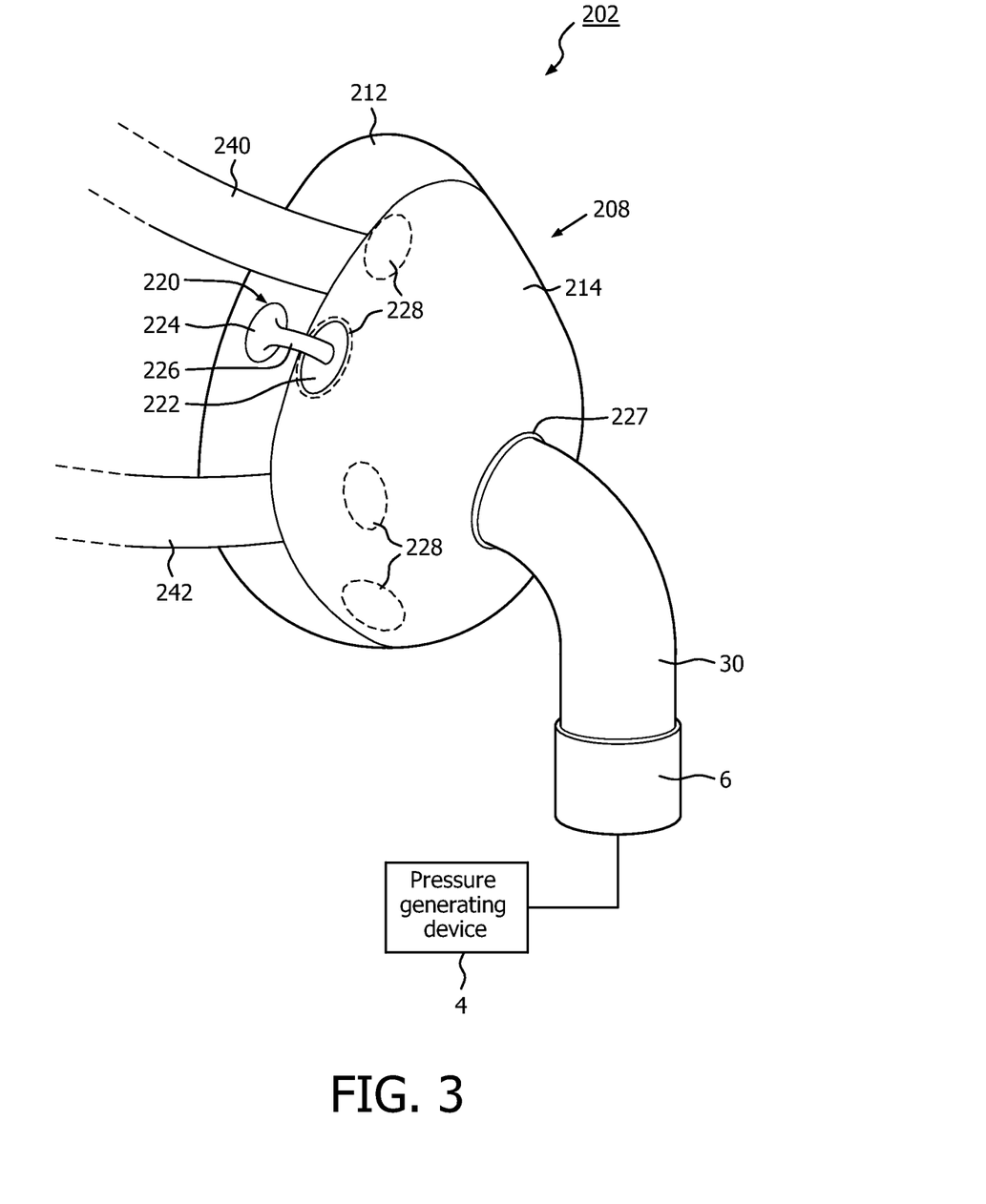
FIG. 3 is a schematic/isometric view of a system adapted to provide a regimen of respiratory therapy to a patient according to another exemplary embodiment.

FIG. 3 is a schematic/isometric view of a system 202 adapted to provide a regimen of respiratory therapy to a patient according to another exemplary embodiment of the present invention. System 202 includes pressure generating device 4, delivery conduit 6, and elbow conduit 30 which are described above with respect to FIG. 1. System 202 further includes an alternative patient interface device 208, which is described in detail below. Delivery conduit 6 is structured to communicate the flow of breathing gas from pressure generating device 4 to patient interface device 208.

Patient interface device 208 includes a patient sealing assembly, which in the illustrated embodiment is a nasal mask. However, any type of patient sealing assembly, such as a nasal/oral mask or a full face mask, may be substituted for the nasal mask while remaining within the scope of the present invention. The mask includes a sealing cushion member 212 which is coupled to a faceplate 214. In the illustrated embodiment, sealing cushion member 212 is defined from a unitary piece of soft, flexible, cushiony, elastomeric material, such as, without limitation, silicone, an appropriately soft thermoplastic elastomer, a closed cell foam, or any combination of such materials.

Faceplate 214 is fluidly coupled to pressure generating device 4 through elbow conduit 30 and delivery conduit 6. In the illustrated embodiment, faceplate 214 is made of a rigid or semi-rigid material, such as, without limitation, an injection molded thermoplastic or silicone, and includes an orifice 227 on a front end thereof and a number of landings 228 on a rear end thereof. Orifice 227 is structured to receive elbow conduit 30. The purpose of landings 228 is described below.

Patient interface device 208 further includes an upper headgear strap 240 and a lower headgear strap 242. Upper headgear strap 240 and lower headgear strap 242 form at least a portion of a headgear assembly for securing patient interface device 208 to the head of a patient.

Patient interface device 208 still further includes a sealing device 220. Sealing device 220 can attach to patient interface device 208 at any of landings 228. Landings 228 can be integrally formed in faceplate 214 or on an exterior of faceplate 214. In particular, sealing device 220 includes a base 222, an end portion 224, and an arm 226 provided between base 222 and end portion 224. In the exemplary embodiment, end portion 224 and arm 226 form a T-shaped member.

Figure 4:
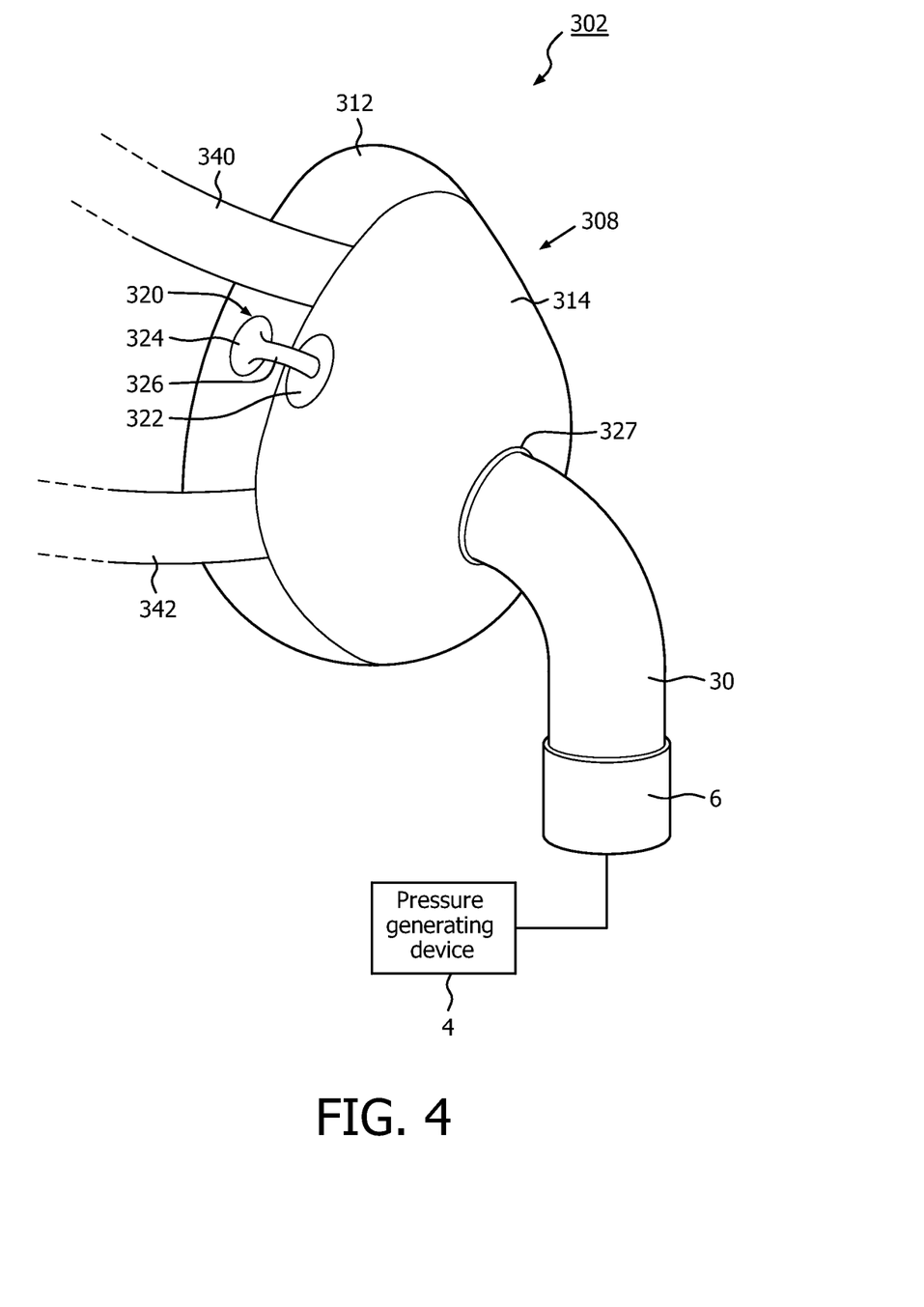
FIG. 4 is a schematic/isometric view of a system 4 adapted to provide a regimen of respiratory therapy to a patient according to another exemplary embodiment.

FIG. 4 is a schematic/isometric view of a system 302 adapted to provide a regimen of respiratory therapy to a patient according to another exemplary embodiment of the present invention. System 302 includes pressure generating device 4, delivery conduit 6, and elbow conduit 30 which are described above with respect to FIG. 1. System 302 further includes an alternative patient interface device 308, which is described in detail below. Delivery conduit 6 is structured to communicate the flow of breathing gas from pressure generating device 4 to patient interface device 308.

Patient interface device 308 includes a patient sealing assembly, which in the illustrated embodiment is a nasal mask. However, any type of patient sealing assembly, such as a nasal/oral mask or a full face mask, may be substituted for the nasal mask while remaining within the scope of the present invention. The mask includes a sealing cushion member 312 which is coupled to a faceplate 314. In the illustrated embodiment, sealing cushion member 312 is defined from a unitary piece of soft, flexible, cushiony, elastomeric material, such as, without limitation, silicone, an appropriately soft thermoplastic elastomer, a closed cell foam, or any combination of such materials.

Faceplate 314 is fluidly coupled to pressure generating device 4 through elbow conduit 30 and delivery conduit 6. In the illustrated embodiment, faceplate 314 is made of a rigid or semi-rigid material, such as, without limitation, an injection molded thermoplastic or silicone, and includes an orifice 327 on a front end thereof and a number of landings 328 on a rear end thereof. Orifice 327 is structured to receive elbow conduit 30. The purpose of landings 328 is described below.

Patient interface device 308 further includes an upper headgear strap 340 and a lower headgear strap 342. Upper headgear strap 340 and lower headgear strap 342 form at least a portion of a headgear assembly for securing patient interface device 8 to the head of a patient.

Patient interface device 308 still further includes sealing device 320. Sealing device 320 includes a base 322, an end portion 324, and an arm 326 provided between base 322 and end portion 324. In the embodiment illustrated in FIG. 4, base 322 includes an adhesive to attach sealing device 320 to faceplate 314. The adhesive may be, without limitation, a permanent adhesive which is intended to be used to attach sealing device 320 to faceplate 314 once, a semi-permanent adhesive which is intended to be used to attach sealing device 320 to faceplate 314 a limited number of times, or a reusable adhesive which is intended to be used to attach sealing device 320 to faceplate 314 numerous times. Additionally, when sealing device 320 is attached to faceplate 314 by an adhesive, sealing device 314 may be used with any suitable patient interface device.

Figure 5A:
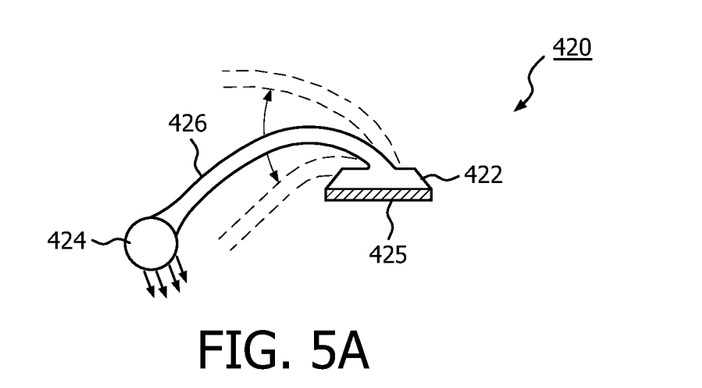
FIGS. 5A-C illustrate sealing devices according to various exemplary embodiments.
Figure 5B:
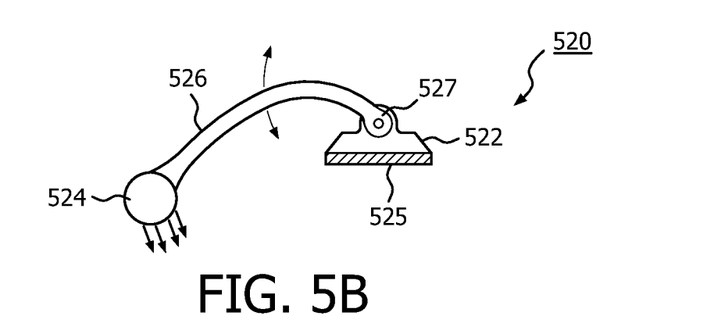
Figure 5C:
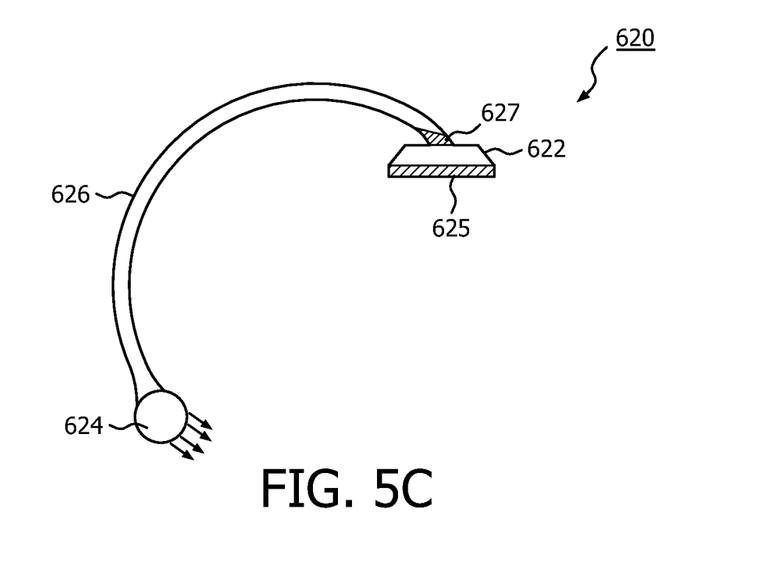

FIGS. 5A-C illustrate sealing devices (420, 520, 620) according to various particular embodiments of the invention. As seen below, the sealing devices are described including a base having an adhesive, and thus are readily useable in the embodiment of FIG. 4. However, it will be understood that that is meant to be exemplary only, and that the structures shown in FIGS. 5A-C may be adopted for use in the embodiments of FIGS. 1-3.

Referring to FIG. 5A, sealing device 420 includes a base 422, an arm 426, and an end portion 424. Additionally, sealing device 426 includes an adhesive 425 attached to base 422. In sealing device 420 illustrated in FIG. 5A, arm 426 includes a metallic material. Arm 426 is adjusted by bending arm 426 such that end portion 424 applies pressure to a desired area of a cushion member.

Referring to FIG. 5B, sealing device 520 includes a base 522, an arm 526, and an end portion 524. Additionally, sealing device 520 includes an adhesive 525 attached to base 522. In sealing device 520 illustrated in FIG. 5B, arm 526 is connected to base 522 by a ratchet 527 or some other hinging device that is selectively lockable in a number of positions. Arm 526 is adjusted by moving arm 526 to operate ratchet 527 such that end portion 524 applies pressure to a desired area of a cushion member.

Referring to FIG. 5C, sealing device 620 includes a base 622, an arm 626, and an end portion 624. Additionally, sealing device 620 includes an adhesive 625 attached to base 622. In sealing device 620 illustrated in FIG. 5C, arm 626 is connected to base 622 by a permeable hinge 627 such as, for example, silicone. Arm 626 is biased/preloaded by hinge 627 such that end portion 624 applies pressure to a desired area of a cushion member when sealing device 620 is attached to a patient interface device. Hinge 627 is permeable so as to permit a limited movement of arm 626 while still applying pressure to the desired area of the cushion member.

Figure 6A:
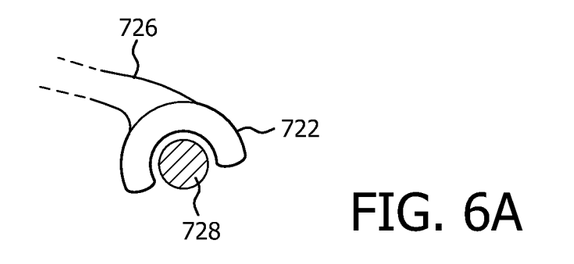
FIGS. 6A-D illustrate bases of sealing devices according to various exemplary embodiments.

FIGS. 6A-D illustrate bases of sealing devices according to various particular embodiments of the invention that may be used in one or more of systems 2, 102, 202, and 302 described herein. Referring to FIG. 6A, a base 722 is attached to an arm 726 and is c-shaped and configured to snap onto a ridge 728 provided on/in a faceplate.

Figure 6B:
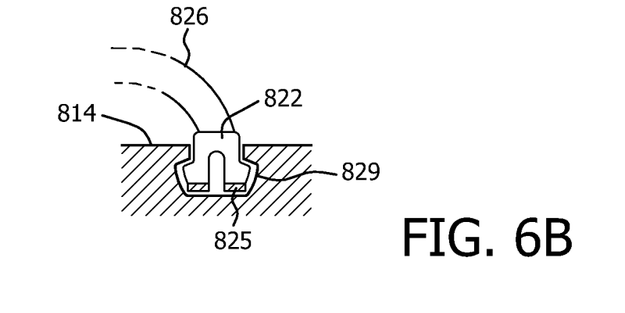

FIG. 6B illustrates a base 822 connected to an arm 826 and configured to snap into a groove 829 formed in a faceplate 814. Base 822 includes two arms each having a protruding tooth and which engage with an interior of groove 829 to snap into groove 829. Base 822 also includes tacky material 825 such as, for example, silicone, which prevents or reduces movement of base 825 within groove 829.

Figure 6C:
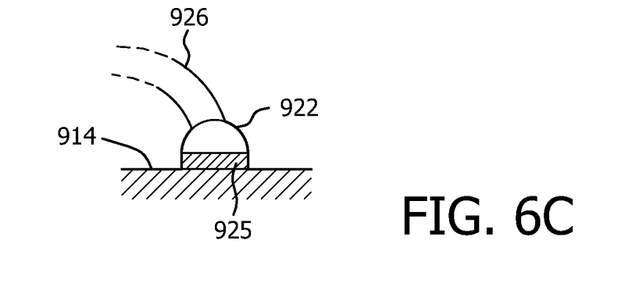

FIG. 6C illustrates a base 922 connected to an arm 926. Base 922 includes an adhesive 925 which is used to adhesively attach base 922 to a faceplate 914.

Figure 6D:
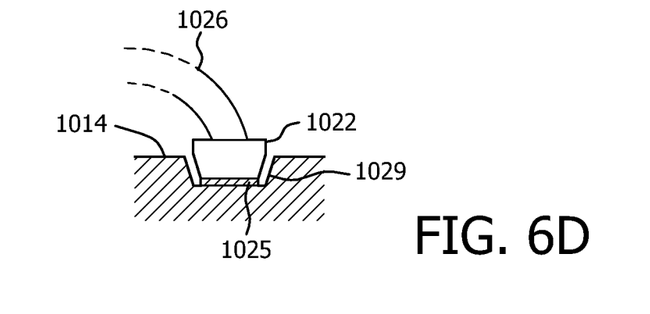

FIG. 6D illustrates a base 1022 connected to an arm 1026 and configured to be inserted into a groove 1029 formed in a faceplate 1014. Base 1022 includes adhesive 1025 to adhesively attach base to an interior of groove 1029.

Figure 7A:
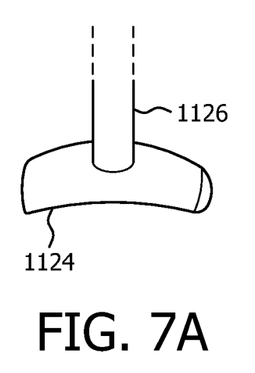
FIGS. 7A-J illustrate end portions of sealing devices according to various exemplary embodiments.

FIGS. 7A-J illustrate end portions of sealing devices according to various particular embodiments of the invention that may be used in one or more of systems 2, 102, 202, and 302 described herein. Referring to FIG. 7A, an end portion 1124 is connected to an arm 1126 and has a shape of a curved paddle. The curved paddle shape accommodates for cushion member geometry around a right mouth corner of a patient.

Figure 7B:
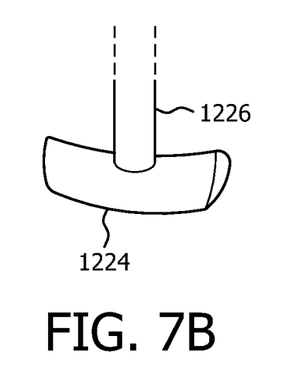

FIG. 7B illustrates an end portion 1224 connected to an arm 1226 and having a shape of a reverse curved paddle. The reverse curved paddle shape accommodates for cushion member geometry around a left mouth corner of a patient.

Figure 7C:
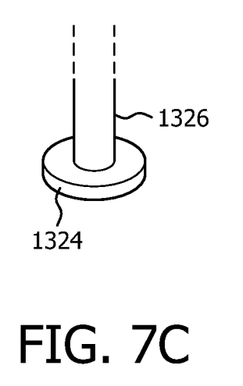

FIG. 7C illustrates an end portion 1324 connected to an arm 1326 and having a shape of a flat disk. The flat disk shape allows end portion 1324 to apply a point force to a cushion member. Additionally, end portion 1324 may include an adhesive.

Figure 7D:
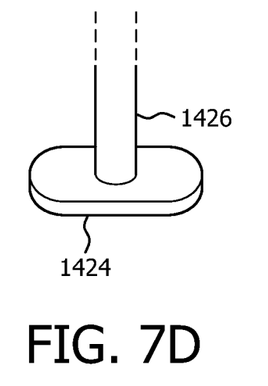

FIG. 7D illustrates an end portion 1424 connected to an arm 1426 and having a shape of an elongated flat disk. The elongated flat disk shape allows end portion 1424 to apply a distributed force to a cushion member. Additionally, end portion 1426 may include an adhesive.

Figure 7E:
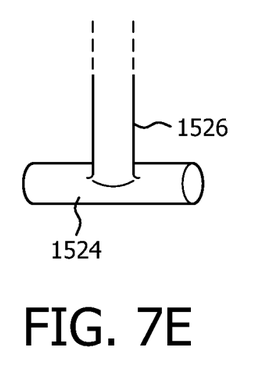

FIG. 7E illustrates an end portion 1524 connected to an arm 1526 and having a cylindrical shape. The cylindrical shape does not need to pivot to apply pressure to a cushion member.

Figure 7F:
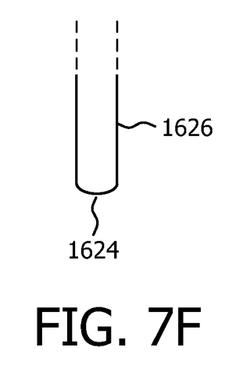

FIG. 7F illustrates an end portion 1624 connected to an arm 1626. End portion 1624 is an extension of arm 1626 and is configured to apply a point force to a cushion member. End portion 1624 can be used, for example, when there is a small leak in a specific area of a cushion member.

Figure 7G:
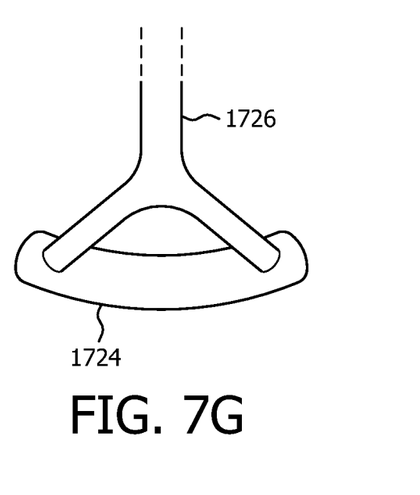

FIG. 7G illustrates an end portion 1724 connected to an arm 1726. Arm 1726 has a y-shape where it connects to end portion 1724 and end portion 1724 has an elongated shape. End portion 1724 is configured to apply a distributed force to a cushion member. End portion 1724 and arm 1726 can be used, for example, to address leaks in an area of a cushion member around a chin of a patient.

Figure 7H:
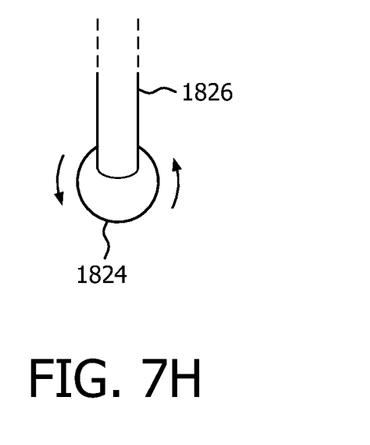

FIG. 7H illustrates an end potion 1824 connected to an arm 1826 and having a form of a ball in socket. End portion 1824 is thus able to rotate and remain in contact with a cushion member as it is moved across the cushion member.

Figures 7I, 7J:
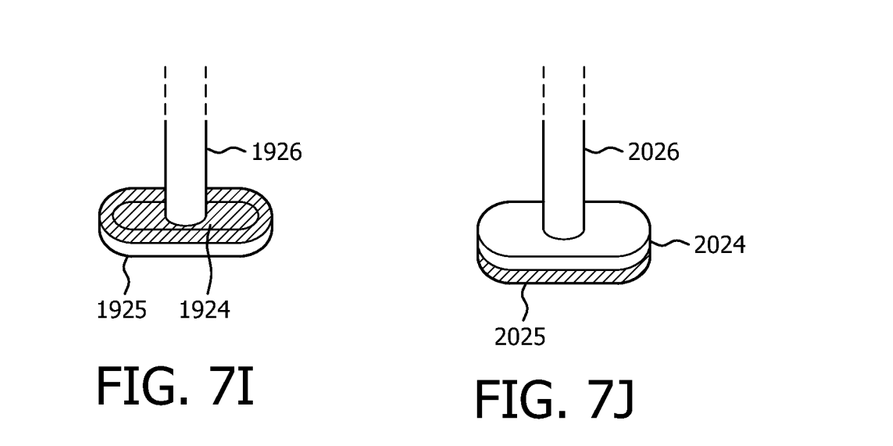

FIG. 7I illustrates an end portion 1924 connected to an arm 1926. End portion 1924 is surrounded by a tacky material 1925 such as, for example, silicone. Tacky material 1925 keeps end portion 1924 in contact with a cushion member. Additionally, tacky material 1925 can increase the comfort of a person adjusting a sealing device by providing padding over end portion 1924.

FIG. 7J illustrates an end portion 2024 connected to an arm 2026. End portion 2024 has a tacky material 2025 such as, for example, silicone, attached to a bottom surface. Tacky material 2025 keeps end portion 2024 in contact with a cushion member.

It is contemplated that the bases, arms, and end portions described above may be provided in any combination in a sealing device for use in, for example and without limitation, systems 2, 102, 202, and/or 302 without departing from the scope of the present invention.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A sealing device comprising:
    a base adapted to attach at any of a plurality of positions on a faceplate of a patient interface device;
    an arm having a first end coupled to the base; and
    an end portion connected to a second end of the arm and adapted to abut against and apply pressure to an area of a cushion member attached to the faceplate of the patient interface device when the base is attached at any of the plurality of positions on the patient interface device, wherein the arm is structured to bend such that the end portion moves with respect to the base to abut against and apply pressure to the area of the cushion.

2. The sealing device according to claim 1, wherein the base is adapted to attach to a ridge included on the faceplate.

3. The sealing device according to claim 2, wherein the base has a c-shape adapted to snap onto the ridge.

4. The sealing device according to claim 1, wherein the base is adapted to be inserted into a groove formed in the faceplate.

5. The sealing device according to claim 4, wherein the base is adapted to snap into the groove.

6. The sealing device according to claim 1, wherein the base includes an adhesive surface configured to attach to the faceplate.

7. The sealing device according to claim 1, wherein the base is adapted to attach to any one of a plurality of landings formed in the faceplate.

8. The sealing device according to claim 1, wherein the arm includes metallic material.

9. The sealing device according to claim 1, wherein the arm is coupled to the base by a ratchet.

10. The sealing device according to claim 1, wherein the arm is coupled to the base by a hinge including a pliable material.

11. The sealing device according to claim 1, wherein the end portion includes a tacky material.

12. A patient interface device comprising:
    a cushion member adapted to fluidly couple with a pressure generating device and adapted to contact a patient;
    a faceplate adapted to attach to the cushion member; and
    a sealing device including:
        a base adapted to attach at any of a plurality of positions on the faceplate;
        an arm having a first end connected to the base; and
        an end portion connected to a second end of the arm and adapted to abut against and apply pressure to an area of the cushion member when the base is attached at any of the plurality of positions on the patient interface device,
        wherein the arm is structured to bend such that the end portion moves with respect to the base to abut against and apply pressure to the area of the cushion.

13. The patient interface device according to claim 12, wherein the faceplate is adapted to fluidly couple with the pressure generating device.

14. The patient interface device according to claim 13, wherein the faceplate includes a ridge and the base is adapted to attach to the ridge.

15. The patient interface device according to claim 14, wherein the base is adapted to snap onto the ridge.

16. The patient interface device according to claim 13, wherein the faceplate includes a groove and the base is adapted to be inserted into the groove.

17. The patient interface device according to claim 16, wherein the base is configured to snap into the groove.

18. The patient interface device according to claim 13, wherein the base includes an adhesive surface configured to attach to the faceplate.

19. The patient interface device according to claim 13, wherein the faceplate includes a plurality of landings formed therein and the base is configured to attach to any one of the landings.

20. The patient interface device according to claim 12, wherein the arm includes metallic material.

21. The patient interface device according to claim 12, wherein the arm is coupled to the base by a ratchet.

22. The patient interface device according to claim 12, wherein the arm is coupled to the base by a hinge including pliable material.

23. The patient interface device according to claim 12, wherein the end portion includes a tacky material.

* * * * *